United States Patent
Tseggai et al.

(10) Patent No.: US 7,582,302 B2
(45) Date of Patent: Sep. 1, 2009

(54) NEEDLE-FREE ADMINISTRATION OF FELV VACCINES

(75) Inventors: Tesfai Tseggai, Athens, GA (US); Maria Camila Pardo, Athens, GA (US); Alton Timothy Leard, Lavonia, GA (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 11/146,299

(22) Filed: Jun. 6, 2005

(65) Prior Publication Data

US 2006/0034867 A1 Feb. 16, 2006

Related U.S. Application Data

(60) Provisional application No. 60/576,771, filed on Jun. 4, 2004.

(51) Int. Cl.
*A61K 39/12* (2006.01)
*A61K 39/21* (2006.01)
*A61K 39/42* (2006.01)
*A61K 39/275* (2006.01)
*C12P 19/34* (2006.01)
*C12N 15/00* (2006.01)
*C12N 15/64* (2006.01)

(52) U.S. Cl. ............... 424/207.1; 424/148.1; 424/187.1; 424/199.1; 424/204.1; 424/232.1; 435/91.1; 435/91.4; 435/91.33; 435/320.1

(58) Field of Classification Search ........................ None
See application file for complete search history.

(56) References Cited

U.S. PATENT DOCUMENTS 5,374,424 A * 12/1994 Kelsey et al. ............ 424/202.1
5,756,103 A * 5/1998 Paoletti et al. ........... 424/199.1

OTHER PUBLICATIONS

Konishi et al., Evidence for antigen production in muscles by dengue and Japanese encephalitis DNA vaccines and a relation to their immunogenicity in mice, Vaccine, 2003, vol. 21, p. 3713-3720.*
Tartaglia et al., Protection of Cats against Feline Leukemia Vieus by Vaccination with a Canarypox Virus Recombinant, ALVAC-FL, Journal of Virology, Apr. 1993, vol. 67, No. 4, p. 2370-2375.*
Dawson et al., A field trail access the effect of vaccination against feline herpesvirus, feline calicivirus and feline panleucopenia virus in 6-week-old kittens, Journal of Feline Medicine and Surgery, 2001, vol. 3, p. 17-22.*
Jackson et al. Safety and immunogenicity of varying dosages of trivalent inactivated influenza vaccine administered by needle-free jet injectors. Vaccine, 2001, vol. 19, No. 32, pp. 4703-4709.*
Aguiar et al. Vaccine, 2002, vol. 20, No. 1-2, pp. 275-280.*
Pertmer et al. Vaccine, 1995, vol. 13, No. 15, pp. 1427-1430.*
Epstein et al., "Safety, Tolerability, and Lack of Antibody Responses After Administration of a PfCSP DNA Malaria Vaccine via Needle or Needle-Free Jet Injection, and Comparison of Intramuscular and Combination Intramuscular/Intradermal Routes", Human Gene Therapy 13:1551-1560 (Sep. 1, 2002).

Haensler et al., "Intradermal DNA immunization by using jet-injectors in mice and monkeys", Vaccine 17 (1999) 628-638.
McKercher & Bachrach, "A Foot-and-Mouth Disease Vaccine for Swine", Can. J. comp. Med., vol. 40, Jan. 1976, pp. 67-74.
Poulet et al., "Efficacy of a canarypox virus-vector vaccine against feline leukaemia", Veterinary Record (2003) 153, 141-145.
Schrijver et al., "Comparison of DNA application methods to reduce BRSV shedding in cattle", Vaccine 1998 vol. 16, No. 2/3, pp. 130-134.
Tartaglia et al., "Protection of Cats against Feline Leukemia Virus by Vaccination with a Canarypox Virus Recombinant, ALVAC-FL", Journal of Virology, Apr. 1993, pp. 2370-2375.
Van Rooij et al., "Effect of vaccination route and composition of DNA vaccine on the induction of protective immunity against pseudorabies infection in pigs", Veterinary Immunology and Immunopathology 66 (1998) 113-126.
Flynn JN, Dunham SP, Watson V, Jarrett O. Longitudinal analysis of feline leukemia virus-specific cytotoxic T lymphocytes: correlation with recovery from infection. J Virol. Mar. 2002;76(5):2306-15.
Hawks DM, Legendre AM, Rohrbach BW, Sebring R, Chavez L, Chu HJ, Acree WM. Antibody response of kittens after vaccination followed by exposure to feline leukemia virus-infected cats. JAMA. Nov. 1991;199(10):1463-1469.
Schultz J, Dollenmaier G, Molling K. Update on antiviral DNA vaccine research (1998-2000). Intervirology. 2000;43(4-6):197-217.
McKercher PD, Bachrach HL. A foot-and-mouth disease vaccine for swine. Can J Comp Med. Jan. 1976;40(1):67-74.
Pedersen et al., Possible immunoenhancement of persistent viremia by feline leukemia virus envelope glycoprotein vaccines in challenge-exposure situations where whole inactivated virus vaccines were protective. Vet Immunol Immunopathol. Feb. 1986;11 (2):123-48.
Couch, Assessment of Immunity to Influenza Using Artificial Challenge of Normal Volunteers with Influenza Virus, International Symposium on Immunity to Infections of the Respiratory System in Man and Animals, London 1974, Develop. Biol. Standard, vol. 28, pp. 295-306.
Flynn et al., Feline Leukaemia Virus: Protective Immunity is Mediated by Virus-Specific Cytotoxic T Lymphocytes, Immunology 2000, vol. 101, pp. 120-125.
Garch et al., Feline Leukemia Virus (FeLV)-Specific IFNγ+ T-Cell Responses Are Induced in Cats Following Transdermal Vaccination With a Recombinant FeLV Vaccine, Intern. J. Appl. Res. Vet. Med., vol. 4, No. 2, 2006, pp. 100-108.
Hawks et al., Antibody Response of Kittens After Vaccination Followed by Exposure to Feline Leukemia Virus-Infected Cats, JAVMA, vol. 199, No. 10, Nov. 15, 1991, pp. 1463-1469.

(Continued)

*Primary Examiner*—Bruce Campell
*Assistant Examiner*—Sharon Hurt
(74) *Attorney, Agent, or Firm*—Judy Jarecki-Black; Merial Limited; Thomas Kowalski, Esq.

(57) ABSTRACT

The invention provides a novel method of vaccination of an animal of the felidae family against feline leukemia. The FeLV recombinant vaccine based on viral vector with the aid of a liquid jet needle-free injector can result in distribution of the vaccine essentially in the dermis and the hypodermis of the animal.

18 Claims, 1 Drawing Sheet

OTHER PUBLICATIONS

United States Patent and Trademark Office, Before the Board of Patent Appeals and Interferences, Ex parte Alan N. Houghton et al., Appeal 2008-4425, U.S. Appl. No. 09/996,128, Technology Center 1600, Decided Dec. 11, 2008.

Jacobs DE, Arakawa A, Courtney CH, Gemmell MA, McCall JW, Myers GH, Vanparijs O; World Association for the Advancement of Veterinary Parasitology (W.A.A.V.P.) guidelines for evaluating the efficacy of anthelmintics for dogs and cats, Vet Parasitol. Apr. 1994;52(3-4):179-202.

* cited by examiner

NEEDLE-FREE ADMINISTRATION OF FELV VACCINES

INCORPORATION BY REFERENCE

This application which claims benefit of U.S. provisional patent application Ser. No. 60/576,771 filed Jun. 4, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The invention provides a method of vaccination of an animal of the felidae family against feline leukemia.

BACKGROUND OF THE INVENTION

FeLV is a common infection of domestic cats throughout the world and a cause of significant morbidity and mortality. The prevalence of antigenaemia may vary from 1 to 5 per cent in healthy cats to 15 to 30 per cent in sick cats (Hosie M. J. et al., Veterinary Records, 1989, 128, 293-297; Braley J., Feline Practice, 1994, 22, 25-29; Malik R. et al., Australian Veterinary Journal, 1997, 75, 323-327; Arjona A. et al., Journal of Clinical Microbiology, 2000, 38, 3448-3449). The virus may establish a life-long infection characterized by a persistent viraemia and a fatal outcome. Most FeLV-related diseases occur in persistently infected animals, and they are always serious and mostly fatal. Among the most frequently diagnosed conditions are lymphomas, myeloid leukaemias, immunodeficiency and non-regenerative anaemia. The infection can be controlled by the identification and isolation of persistently viraemic cats, which are the source of the infection, and vaccines have also helped to prevent the virus spreading. Several FeLV vaccines are available; most of them contain either inactivated virus or recombinant subunits. Their efficacy is controversial (Sparkes A. H., Journal of Small Animal Practice, 1997, 38, 187-194). Vaccine breakdowns have been observed and there is a need for an improvement in efficacy and particularly for more evidence of protection in field conditions. An alternative way would be to use recombinant viral vector. The canarypox virus vector and especially the ALVAC vector have been tested for the expression of FeLV genes (Tartaglia J. et al., Journal of Virology, 1993, 67, 2370-2375; Poulet H. et al., Veterinary Record, 2003, 153, 141-145). A commercial recombinant FeLV vaccine is also available (EURIFEL® FeLV, Merial).

There is thus a general need for an improvement in efficacy and safety of the FeLV vaccines.

Generally the efficacy of a vaccine is increased by the administration of a higher dose of immunogens, or by the formulation of the vaccine with adjuvants, or a combination of both.

The administration of a higher dose of immunogens increases dramatically the cost of the vaccine in such a manner that the vaccine becomes too expensive for customers.

In the other way, the formulation of the vaccine with adjuvants renders the vaccine more efficacious and allows sometime to reduce the amount of immunogens. However adjuvanted vaccines induce a higher rate of local adverse reactions than non-adjuvanted ones (Gobar et al., JAVMA, 2002, 220 (10), 1477-1482) and thereby increase the risk of vaccine-associated fibrosarcomas at the injection site (Baker R. J., Feline Practice, 1998, 26(5), 18-20).

It has also been proposed to use needle-free injectors in veterinary field (WO-A-98/03659; WO-A-92/15330; WO-A-98/03658; van Rooij et al., Vet. Immunol. Immunopathol., 1998, 66(2), 113-126; U.S. Pat. No. 6,451,770; Schrijver et al., Vaccine, 1998, 16(2-3), 130-134). There are however contradictory results in the art (McKercher P. D. et al., Can. J. Comp. Med., 1976, 40, 67-74; Epstein, Hum. Gene Ther., 2002, 13(13), 275-280; Haensler, Vaccine, 1999, 17(7-8), 628-638).

Citation or identification of any document in this application is not an admission that such document is available as prior art to the present invention.

SUMMARY OF THE INVENTION

The objective of the present invention is to provide a new method of vaccination of an animal of the felidae family, which is efficient, easier and less expensive to use, and which leads to increased safety.

This objective is met by administering a FeLV recombinant vaccine based on viral vector with the aid of a liquid jet needle-free injector, ensuring distribution of the vaccine essentially in the dermis and the hypodermis of the animal.

A first object of the present invention is a vaccination method against FeLV, which may comprise the step of administration essentially in the dermis and the hypodermis of an animal of the felidae family an efficient amount of a FeLV recombinant vaccine based on a viral vector using a liquid jet needle-free injector, which administration elicits a safe and protective immune response against FeLV.

Another object is a vaccination kit or set, which may comprise such a liquid jet needle-free injector and at least one vaccine vial containing a FeLV recombinant vaccine based on a viral vector, operatively assembled to perform the administration of the vaccine essentially in the dermis and the hypodermis of an animal of the felidae family and to elicit a safe and protective immune response against FeLV.

Another object of the invention is the use of a recombinant viral vector which may encode and express at least one FeLV immunogen and of an acceptable vehicle or diluent, for the preparation of a liquid vaccine designed to be administered essentially in the dermis and the hypodermis of animals of the felidae family using a liquid jet needle-free injector, and resulting in eliciting a safe and protective immune response against FeLV.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF DRAWINGS

The following Detailed Description, given by way of example, and not intended to limit the invention to specific embodiments described, may be understood in conjunction with the accompanying Figures, incorporated herein by reference, in which.

DETAILED DESCRIPTION

The present invention concerns a vaccination method against FeLV, comprising the step of administration essentially in the dermis and the hypodermis of an animal of the felidae family an efficient amount of a FeLV recombinant vaccine based on a viral vector using a liquid jet needle-free injector, which administration elicits a safe and protective immune response against FeLV.

"Essentially" means what some vaccines may also be found in the epidermis or in the muscles.

A protective immune response is characterized by a significant reduction of the antigenemia after challenge or by significant neutralizing antibody titers. A safe immune response is characterized by the limitation of the side effects linked to the vaccine administration, notably by a significant reduction or by the absence of local injection site reaction and by a significant reduction or by the absence of symptoms, like anorexia and depression following vaccine administration.

An animal of the felidae family encompasses cats, this including new born, kitten, male, female, pregnant female.

The vaccine comprises a recombinant viral vector and an acceptable vehicle or diluent. The recombinant viral vector includes notably herpesvirus, adenovirus and poxvirus such as fowlpox (U.S. Pat. No. 5,174,993; U.S. Pat. No. 5,505,941 and U.S. Pat. No. 5,766,599) or canarypox (U.S. Pat. No. 5,756,103)). The vehicle or diluent includes but is not limited to sterile water, physiological saline, glucose, buffer and the like. The vehicle or diluent may also include polyols, glucides or pH buffering agents. The vehicle or diluent may, for example, also comprise amino acids, peptides, antioxidants, bactericide, bacteriostatic compounds.

The recombinant viral vector encodes and expresses at least one FeLV immunogen, notably FeLV env gene or FeLV env and gag/pol genes. A complete sequence of the FeLV genome can be found in Chen et al., J Virol. 1998 Sep. 72(9): 7048-56, which coupled with routine experimentation enables one of ordinary skill in the art may ascertain the sequence of any FeLV immunogen.

In a preferred aspect of this embodiment, the method of the invention is performed with a recombinant canarypox virus expressing FeLV env or FeLV env and gag/pol genes (e.g. vCP97 construct, see example 53 in U.S. Pat. No. 5,756,103).

As an alternative aspect of the invention, the method of the invention is performed with a recombinant fowlpox virus expressing FeLV env or FeLV env and gag/pol genes.

The invention further encompasses at least one FeLV immunogen contained in a vector molecule or an expression vector and operably linked to a promoter element and optionally to an enhancer.

In an advantageous embodiment, the promoter is the promoter of the cytomegalovirus (CMV) immediate early gene. In another advantageous embodiment, the promoter and/or enhancer elements are oxygen-inducible. Examples of oxygen-inducible promoters and/or enhancers that can be used in the methods of the present invention include, but are not limited to, early growth response-1 (Egr1) promoter (see, e.g., Park et al., J Clin Invest. August 2002; 110(3):403-1), hypoxia-inducible factor (HIF) inducible enhancers (see e.g., Cuevas et al., Cancer Res. Oct. 15, 2003;63(20):6877-84) and Mn-superoxide dismutase (Mn-SOD) promoters (see, e.g., Gao et al., Gene. Oct. 17, 1996;176(1-2):269-70).

In another embodiment, the enhancers and/or promoters include various cell or tissue specific promoters (e.g., muscle, endothelial cell, liver, somatic cell or stem cell), various viral promoters and enhancers and various FeLV immunogen sequences isogenically specific for each animal species. Examples of muscle-specific promoters and enhancers have been described are known to one of skill in the art (see, e.g., Li et al., Gene Ther. December 1999;6(12):2005-11; Li et al., Nat Biotechnol. March 1999;17(3):241-5 and Loirat et al., Virology. Jul. 20, 1999;260(1):74-83; the disclosures of which are incorporated by reference in their entireties).

Promoters and enhancers that may be employed in the present invention include, but are not limited to LTR or the Rous sarcoma virus, TK of HSV-1, early or late promoter of SV40, adenovirus major late (MLP), phosphoglycerate kinase, metallothionein, $\alpha$-1 antitrypsin, albumin, collagenese, elastase I, $\beta$-actin, $\beta$-globin, $\gamma$-globin, $\alpha$-fetoprotein, muscle creatin kinase.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors also included are viral vectors.

The term "recombinant" means a polynucleotide semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

The present invention encompasses a vector expressing a FeLV immunogen or variants or analogues or fragments. Elements for the expression of a FeLV immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. a FeLV immunogen, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6; 312,683; U.S. patent application Ser. No. 920,197, filed Oct. 16, 1986; WO 90/01543; WO 91/11525; WO 94/16716; WO 96/39491; WO 98/33510; EP 265785; EP 0 370 573; Andreansky et al., Proc. Natl. Acad. Sci. USA 1996;93:11313-11318; Ballay et al., EMBO J. 1993;4:3861-65; Felgner et al., J. Biol. Chem. 1994;269:2550-2561; Frolov et al., Proc. Natl. Acad. Sci. USA 1996;93:11371-11377; Graham, Tibtech 1990;8:85-87; Grunhaus et al., Sem. Virol. 1992;3:237-52; Ju et al., Diabetologia 1998;41:736-739; Kitson et al., J. Virol. 1991;65:3068-3075; McClements et al., Proc. Natl. Acad. Sci. USA 1996;93:11414-11420; Moss, Proc. Natl. Acad. Sci. USA 1996;93:11341-11348; Paoletti, Proc. Natl. Acad. Sci. USA 1996;93:11349-11353; Pennock et al., Mol. Cell. Biol. 1984;4:399406; Richardson (Ed), Methods in Molecular Biology 1995;39, "Baculovirus Expression Protocols," Humana Press Inc.; Smith et al. (1983) Mol. Cell. Biol. 1983;3:2156-2165; Robertson et al., Proc. Natl. Acad. Sci. USA 1996;93:11334-11340; Robinson et al., Sem. Immunol. 1997;9:271; and Roizman, Proc. Natl. Acad. Sci. USA 1996;93:11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., human adenovirus, canine adenovirus), herpesvirus (e.g. canine herpesvirus), baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-FeLV immunogens, e.g., non-FeLV immunogens, non-FeLV immunogens peptides or fragments thereof, cytokines, etc. to be expressed by vector or vectors in, or included in, the compositions of the invention.

The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of FeLV immunogens. Advantageously, the vector contains and expresses a polynucleotide that includes, consists essentially of, or consists of a coding region encoding one or more FeLV immunogens a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of a FeLv immunogen or a fragment thereof.

According to another embodiment, the vector or vectors in the preparation comprise, or consist essentially of, or consist of polynucleotide(s) encoding one or more proteins or fragment(s) thereof of a FeLV immunogen, the vector or vectors have expression of the polynucleotide(s). The inventive preparation advantageously comprises, consists essentially of, or consists of, at least two vectors comprising, consisting essentially of, or consisting of, and advantageously also expressing, advantageously in vivo under appropriate conditions or suitable conditions or in a suitable host cell, polynucleotides from different FeLV isolates encoding the same proteins and/or for different proteins, but advantageously for the same proteins. Preparations containing one or more vectors containing, consisting essentially of or consisting of polynucleotides encoding, and advantageously expressing, advantageously in vivo, FeLV peptide, fusion protein or an epitope thereof.

According to one embodiment of the invention, the expression vector is a viral vector, in particular an in vivo expression vector. In an advantageous embodiment, the expression vector is an adenovirus vector. Advantageously, the adenovirus is a human Ad5 vector, an E1-deleted and/ or an E3-deleted adenovirus.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Patent No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807), swinepox, raccoonpox, camelpox, or myxomatosis virus.

According to another embodiment of the invention, the poxvirus vector is a canarypox virus or a fowlpox virus vector, advantageously an attenuated canarypox virus or fowipox virus. In this regard, is made to the canarypox available from the ATCC under access number VR-111. Attenuated canarypox viruses are described in U.S. Pat. No. 5,756,103 (ALVAC) and WO01/05934. Numerous fowipox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the atenuated fowlpox strain TROVAC.

For information on the method to generate recombinants thereof and how to administer recombinants thereof, the skilled artisan can refer documents cited herein and to WO90/

12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766,599 inter alia; as to canarypox mentionis made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

In a particular embodiment the viral vector is an adenovirus, such as a human adenovirus (HAV) or a canine adenovirus (CAV).

In one embodiment the viral vector is a human adenovirus, in particular a serotype 5 adenovirus, rendered incompetent for replication by a deletion in the E1 region of the viral genome, in particular from about nucleotide 459 to about nucleotide 3510 by reference to the sequence of the hAd5 disclosed in Genbank under the accession number M73260 and in the referenced publication J. Chroboczek et al Virol. 1992, 186, 280-285. The deleted adenovirus is propagated in E1-expressing 293 (F. Graham et al J. Gen. Virol. 1977, 36, 59-72) or PER cells, in particular PER.C6 (F. Falloux et al Human Gene Therapy 1998, 9, 1909-1917). The human adenovirus can be deleted in the E3 region, in particular from about nucleotide 28592 to about nucleotide 30470. The deletion in the E1 region can be done in combination with a deletion in the E3 region (see, e.g. J. Shriver et al. Nature, 2002, 415, 331-335, F. Graham et al Methods in Molecular Biology Vol .7: Gene Transfer and Expression Protocols Edited by E. Murray, The Human Press Inc, 1991, p 109-128; Y. Ilan et al Proc. Natl. Acad. Sci. 1997, 94, 2587-2592; U.S. Pat. No. 6,133,028; U.S. Pat. No. 6,692,956; S. Tripathy et al Proc. Natl. Acad. Sci. 1994, 91, 11557-11561; B. Tapnell Adv. Drug Deliv. Rev. 1993, 12, 185-199; X. Danthinne et al Gene Thrapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci (region) eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter), in particular the enhancer/promoter region from about nucleotide −734 to about nucleotide +7 in M. Boshart et al Cell 1985, 41, 521-530 or the enhancer/promoter region from the pCI vector from Promega Corp. The CMV-IE promoter is advantageously of murine or human origin. The promoter of the elongation factor 1α can also be used. In one particular embodiment a promoter regulated by hypoxia, e.g. the promoter HRE described in K. Boast et al Human Gene Therapy 1999, 13, 2197-2208), can be used. A muscle specific promoter can also be used (X. Li et al Nat. Biotechnol. 1999, 17, 241-245). Strong promoters are also discussed herein in relation to plasmid vectors. In one embodiment, a splicing sequence can be located downstream of the enhancer/promoter region. For example, the intron 1 isolated from the CMV-IE gene (R. Stenberg et al J. Virol. 1984, 49, 190), the intron isolated from the rabbit or human β-globin gene, in particular the intron 2 from the b-globin gene, the intron isolated from the immunoglobulin gene, a splicing sequence from the SV40 early gene or the chimeric intron sequence isolated from the pCI vector from Promege Corp. comprising the human β-globin donor sequence fused to the mouse immunoglobulin acceptor sequence (from about nucleotide 890 to about nucleotide 1022 in Genbank under the accession number CVU47120). A poly(A) sequence and terminator sequence can be inserted downstream the polynucleotide to be expressed, e.g. a bovine growth hormone gene, in particular from about nucleotide 2339 to about nucleotide 2550 in Genbank under the accession number BOVGHRH, a rabbit β-globin gene or a SV40 late gene polyadenylation signal.

In another embodiment the viral vector is a canine adenovirus, in particular a CAV-2 (see, e.g. L. Fischer et al. Vaccine, 2002, 20, 3485-3497; U.S. Pat. No. 5,529,780; U.S. Pat. No. 5,688,920; PCT Application No. WO95/14102). For CAV, the insertion sites can be in the E3 region and /or in the region located between the E4 region and the right ITR region (see U.S. Pat. No. 6,090,393; U.S. Pat. No. 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as a canine herpesvirus (CHV) or a feline herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). In one particular embodiment a promoter regulated by hypoxia, e.g. the promoter HRE described in K. Boast et al Human Gene Therapy 1999, 13, 2197-2208), can be used. A poly(A) sequence and terminator sequence can be inserted downstream the polynucleotide to be expressed, e.g. bovine growth hormone or a rabbit β-globin gene polyadenylation signal.

According to a yet further embodiment of the invention, the expression vector is a plasmid vector or a DNA plasmid vector, in particular an in vivo expression vector. In a specific, non-limiting example, the pVR1020 or 1012 plasmid (VI- CAL Inc.; Luke C. et al., Journal of Infectious Diseases, 1997, 175, 91-97; Hartikka J. et al., Human Gene Therapy, 1996, 7, 1205-1217, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding the FeLV immunogen or a variant, analog or fragment thereof, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart M. et al., Cell., 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit b-globin gene (van Ooyen et al., Science, 1979, 206, 337-344).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit b-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

Host cells that can be used in the present invention include, but are not limited to, muscle cells, keratinocytes, myoblasts, Chinese Hamster ovary cells (CHO), vero cells, BHK21, sf9 cells, and the like. It is understood to one of skill in the art that conditions for culturing a host cell varies according to the particular gene and that routine experimentation is necessary at times to determine the optimal conditions for culturing an FeLV depending on the host cell. For example, the vector encoding an FeLV immunogen can be transformed into myoblasts (which can be obtained from muscle tissue from the animal in need of treatment), and the transformed myoblasts can be transplanted to the animal. In another example, keratinocytes can also be transformed with a vector encoding a FeLV immunogen and transplanted into the animal, resulting in secretion of a FeLV immunogen into circulation.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of a FeLV immunogen in a target cell. Determination of the therapeutically effective amount is routine experimentation for one of ordinary skill in the art. In one embodiment, the formulation comprises an expression vector comprising a polynucleotide that expresses a FeLV immunogen and a pharmaceutically or veterinarily acceptable carrier, vehicle or excipient. In an advantageous embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95: about 5 to about 5:about 95, more advantageously about 1: about 1, e.g., 1:1.

The DMRIE or DMRIE-DOPE adjuvant:plasmid weight ratio can be between about 50: about 1 and about 1: about 10, such as about 10: about 1 and about 1:about 5, and advantageously about 1: about 1 and about 1: about 2, e.g., 1:1 and 1:2.

The polymers of acrylic or methacrylic acid are preferably crosslinked, in particular with polyalkenyl ethers of sugars or polyalcohols. These compounds are known under the term carbomer (Pharmeuropa vol. 8, No. 2, June 1996). Persons skilled in the art can also refer to U.S. Pat. No. 2,909,462 describing such acrylic polymers crosslinked with a polyhydroxylated compound having at least 3 hydroxyl groups, preferably not more than 8, the hydrogen atoms of at least three hydroxyls being replaced with unsaturated aliphatic radicals having at least 2 carbon atoms. The preferred radicals are those containing 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are crosslinked with an allyl sucrose or with allylpentaerythritol. Among them, there may be mentioned Carbopol® 974P, 934P and 971 P.

Among the copolymers of maleic anhydride and of alkenyl derivative, the EMA® copolymers (Monsanto) which are copolymers of maleic anhydride and of ethylene, which are linear or crosslinked, for example crosslinked with divinyl ether, are preferred. Reference may be made to J. Fields et al., Nature, 186: 778-780, Jun. 4, 1960.

The proportions of adjuvant which are useful are well known and readily available to the one skilled in the art. By way of example, the concentration of polymers of acrylic or methacrylic acid or of anhydride maleic and alkenyl copolymers in the final vaccine composition will be from 0.01% to 1.5% W/V, more particularly from 0.05 to 1% W/V, preferably from 0.1 to 0.4% W/V.

Optionally the vaccine used according to the method of the invention may contain a cytokine. The cytokine may be present as a protein or as a gene encoding this cytokine inserted into a recombinant viral vector. The cytokines may be selected among the feline cytokines, e.g. feline interleukine 18 (fIL-18) (Taylor S. et al., DNA Seq., 2000, 10(6), 387-394), fIL-16 (Leutenegger C. M. et al., DNA Seq., 1998, 9(1), 59-63), fIL-12 (Fehr D. et al., DNA Seq., 1997, 8(1-2), 77-82; Imamura T. et al., J. Vet. Med. Sci., 2000, 62(10), 1079-1087) and feline GM-CSF (Granulocyte-Macrophage Colony-Stimulating Factor) (GenBank AF053007).

In a specific embodiment, the pharmaceutical composition is directly administered in vivo, and the encoded product is expressed by the vector in the host. The methods of in vivo delivery a vector encoding a FeLV immunogen (see, e.g., U.S. Pat. No. 6,423,693; patent publications EP 1052286, EP 1205551, U.S. patent publication 20040057941, WO 9905300 and Draghia-Akli et al., Mol Ther. December 2002; 6(6):830-6; the disclosures of which are incorporated by reference in their entireties) can be modified to deliver the FeLV immunogen of the present invention to a cat. The in vivo delivery of a vector encoding the FeLV immunogen described herein can be accomplished by one of ordinary skill in the art given the teachings of the above-mentioned references.

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

In the case of therapeutic and/or pharmaceutical compositions based on a plasmid vector, a dose can comprise, consist essentially of or consist of, in general terms, about in 1 mg to about 2000 mg, advantageously about 50 mg to about 1000 mg and more advantageously from about 100 μg to about 800 μg of plasmid expressing a FeLV immunogen. When the therapeutic and/or pharmaceutical compositions based on a plasmid vector is administered with electroporation the dose of plasmid is generally between about 0.1 µg and 1 mg, advantageously between about 1 µg and 100 µg, advantageously between about 2 µg and 50 µg. The dose volumes can be between about 0.1 and about 2 ml, advantageously between about 0.2 and about 1 ml. These doses and dose volumes are suitable for the treatment of felines and other mammalian target species such as equines and canines.

The therapeutic and/or pharmaceutical composition contains per dose from about $10^4$ to about $10^{11}$, advantageously from about $10^5$ to about $10^{10}$ and more advantageously from about $10^6$ to about $10^9$ viral particles of recombinant adenovirus expressing a FeLV immunogen. In the case of therapeutic and/or pharmaceutical compositions based on a poxvirus, a dose can be between about $10^2$ pfu and about $10^9$ pfu. The pharmaceutical composition contains per dose from about $10^5$ to $10^9$, advantageously from about $10^6$ to $10^8$ pfu of poxvirus or herpesvirus recombinant expressing a FeLV immunogen.

The dose volume of compositions for target species that are mammals, e.g., the dose volume of feline compositions, based on viral vectors, e.g., non-poxvirus-viral-vector-based compositions, is generally between about 0.1 to about 2.0 ml, preferably between about 0.1 to about 1.0 ml, and more preferably between about 0.5 ml to about 1.0 ml.

t should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Biojector or Vitajet apparatus (Bioject, Oreg., USA)). Another approach to administer plasmid compositions is to use electroporation (see, e.g. S. Tollefsen et al. Vaccine, 2002, 20, 3370-3378; S. Tollefsen et al. Scand. J. Immunol., 2003, 57, 229-238; S. Babiuk et al., Vaccine, 2002, 20, 3399-3408; PCT Application No. WO99/01158). In another embodiment, the plasmid is delivered to the animal by gene gun or gold particle bombardment. In an advantageous embodiment, the animal is a vertebrate. In a more advantageous embodiment, the vertebrate is a cat.

Liquid jet needle-free injectors are devices performing injections of a certain amount of liquid under high pressure through a minute orifice. Mechanical specifications of the injector may be adjusted or selected in order to control the depth of penetration into tissues. Administrations of a liquid using a syringe or a needle-free injector end up in a different distribution of the liquid in the tissues. Using a syringe end up in a localized bolus or pool. Using an injector end up in a diffused distribution in the layers of the targeted tissues, as illustrated in WO-A-01/13975.

The depth of penetration is mainly controlled by the liquid pressure. This liquid pressure is depending upon the mechanical specifications of the injector, such as the strength of spring or any other propulsion means and the diameter of the piston and the nozzle orifice. This is readily available to the one skilled in the art.

The depth of injection may be easily determined by the dissection of the tissue at the injection site (corresponding preferably to the location where the vaccine is going to be administered, and the test is advantageously performed on an animal of the same species and age than the population to be vaccinated) after the administration of a colored liquid having preferably the same viscosity than the intended vaccine. This test may be performed directly with the intended vaccine containing further a dye. This test allows the one skilled in the art to adjust the mechanical specifications of an injector.

The needle-free injector may be equipped with a head comprising one or several nozzles. The use of several nozzles allows to increase the dispersion pattern of the vaccine over a larger area. There can be from 1 to 10 nozzles, preferably from 1 to 6.

Several injectors are available in the commerce. The Vitajet™3 (Bioject Inc.) is particularly adapted to the method according to the invention.

It is advantageous to use an injector equipped with means allowing to fit to the injector directly a standard vial or ampoule. In addition, the vaccine vial may comprise several vaccine doses allowing several shots of vaccine and/or vaccination of several animals using the injector and the same vial. Thus, the injector is preferably able to perform successive injections from a same vial.

The invention also relates to a method to stimulate the immune response of a vertebrate. In one embodiment, the vertebrate is a bird, cat, cow, dog, fish, goat, horse, human, mouse, monkey, pig, rat or sheep. In a more advantageous embodiment, the vertebrate is a cat.

In one aspect of the invention, vaccination against FeLV can be associated with a vaccination against another feline disease. The vaccine comprises the viral vector according to the invention and a vaccine component able to protect against these other diseases, notably feline herpesvirus disease, feline calicivirus disease, feline panleukopenia, parainfluenza virus type 2 disease, feline immunodeficiency disease, and chlamydiosis.

The volume of dose injected may be from about 0.1 ml to about 1.0 ml, preferably about 0.1 ml to about 0.8 ml, more preferably from about 0.2 ml to about 0.5 ml, and in a preferred use the volume of dose injected may be 0.25 ml. By definition, the volume of one dose means the total volume of vaccine administered at once to one animal.

The vaccine may contain from about $10^{4.5}$to about $10^{8.0}$ $TCID_{50}$/dose (50% tissue culture infective dose per dose of vaccine) and preferably from about $10^{5.5}$ to about $10^{6.5}$ $TCID_{50}$/dose.

Optionally, the administration can be repeated, as booster administration, at suitable intervals if necessary or desirable, e.g. about from 2 to about 8 weeks after the first administration, and preferably about from 3 to about 5 weeks after the first administration. A booster administration can also be repeated every year.

Another object of the invention is the use of an efficient amount of a recombinant viral vector encoding and expressing at least one FeLV immunogen as described above and of an acceptable vehicle or diluent, for the preparation of a liquid recombinant viral vaccine designed to be administered essentially in the dermis and the hypodermis of an animal of the felidae family using a liquid jet needle-free injector as described above, and resulting in eliciting a safe and protective immune response against FeLV.

Another object is a vaccination kit or set, comprising such a liquid jet needle-free injector and at least one vaccine vial containing a FeLV recombinant vaccine based on a viral vector as described above, operatively assembled to perform the administration of the vaccine to an animal of the felidae family. The distribution of the vaccine is essentially done in the dermis and the hypodermis.

Such vaccination kit or set is able to elicit a safe and protective immune response against FeLV.

The invention will now be further described by way of the following non-limiting examples.

EXAMPLE 1

Needle-Free Injector Distribution in Kittens 0.3 or 0.5 ml of diluted Chinese ink solution was administered to 8 kittens, from 10 to 14 weeks old.

The injections were done with the Vitajet™ 3 needle-free injector (Bioject Inc.) using nozzles of 0.006 and 0.007 inches diameter and a 100# spring. The injections were administered into the lumbar area or into the quadriceps of kittens without prior shaving.

For the observation of the distribution of the ink, animals were shaved.

The ink was found in the dermis, the subcutaneous area and sometimes, a small amount in the muscle. There was no macroscopic detectable difference between injections done with the 0.006 nozzle and those done with the 0.007 nozzle. The distribution was similar for the different volumes (0.3 and 0.5 ml). The distribution was similar in the lumbar area and in the quadriceps.

Figure 1:
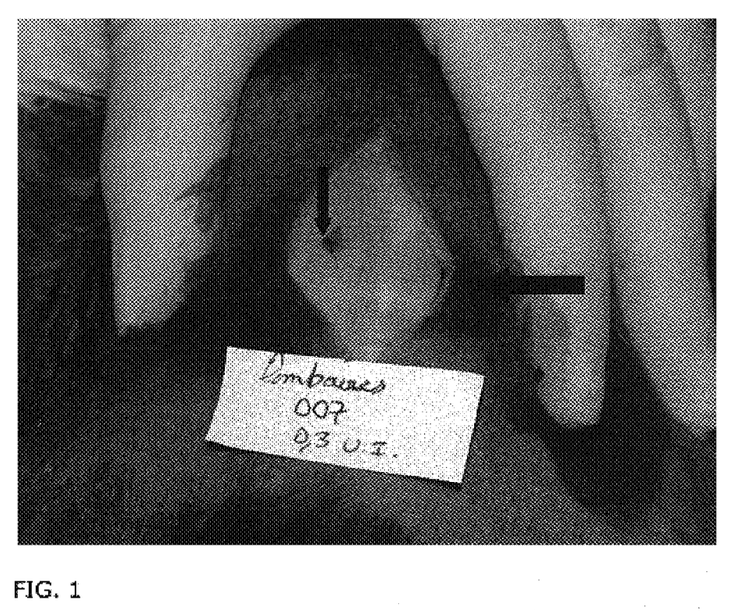
FIG. 1 illustrates the distribution of diluted Chinese ink injected to cats using a needle-free injector. The black arrows indicate areas of dermal and subcutaneous distribution of the ink
Figure 2:
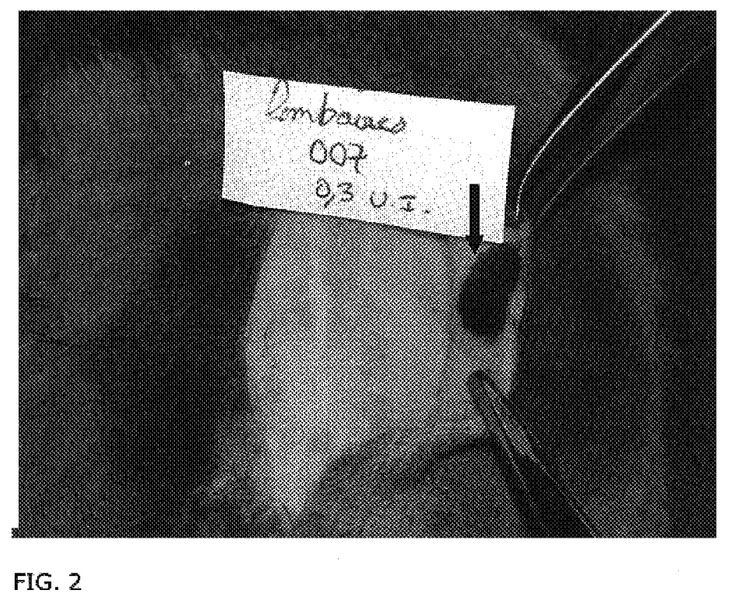
FIG. 2 illustrates the distribution of diluted Chinese ink injected to cats using a needle-free injector. The black arrow indicates areas of intradermal distribution of the ink.

FIGS. 1 and 2 show pictures of these injections and the distribution of the ink.

EXAMPLE 2

Administration of Vaccines in Kittens using Syringe with Needle 40 kittens, 8-9 weeks old, were randomized into two groups of 20 kittens each.

Kittens of group 1 were vaccinated on days 0 and 23 with a vaccine comprising a recombinant canarypox virus vector expressing FeLV env and gag/pol genes (vCP97, see example 53 in U.S. Pat. No. 5,756,103) in sterile water. The injections were administered subcutaneously with a syringe and needle at a volume of 1.0 ml/dose and at $10^{6.6}$ TCID$_{50}$/dose (50% tissue culture infective dose per dose of vaccine).

Kittens of group 2 were given a placebo (1 ml of sterile water) subcutaneously with a syringe and needle on days 0 and 23 to serve as controls.

On day 49, all the kittens were challenged with 1 ml of a virulent strain of FeLV (61E strain, obtained from National Institutes of Health (NIH), USA) at $10^{4.96}$FAID$_{50}$/ml (50% fluorescent antibody infectious dose per milliliter) (0.5 ml orally and 0.25 ml per nostril).

Blood samples were collected the days of vaccination and challenge, and twenty days following challenge and weekly for 4-8 additional weeks. The blood samples were tested for FeLV antigenemia using a commercial kit (Virachek®, Synbiotics Corp.) to detect free, soluble p27 protein. Antigenemia was considered persistent when a kitten tested positive for 3 consecutive weeks or 5 non-consecutive weeks.

FeLV Antigenemia:

In the group 1, seven kittens had persistent antigenemia (65% of protection). In the group 2, 17 kittens had persistent antigenemia, corresponding to 85% of the kittens.

EXAMPLE 3

Needle-Free Injections of Vaccines in Kittens 40 kittens of average age of 9 weeks were randomized into two groups of 20 kittens each.

Kittens of group 1 were vaccinated on days 0 and 22 with recombinant viral vaccine comprising canarypox vector expressing FeLV env and gag/pol genes (vCP97, see example 53 in U.S. Pat. No. 5,756,103) in sterile water.

Group 2 was given a placebo (0.25 ml of sterile water) on day 0 to serve as controls.

All injections were administered into the lateral thigh region via the Vitajet™3 needle-free injector (Bioject Inc.) at a volume of 0.25 ml/dose. The needle-free injector was used with a nozzle of 0.007 inches diameter and a 100# spring.

In the group 1, vaccines were administered at $10^{6.3}$ TCID$_{50}$/dose at first vaccination (V1) and at $10^{5.8}$TCID$_{50}$/dose at second vaccination (V2).

On day 43, all the kittens were challenged with 1 ml of a virulent strain of FeLV (61E strain, obtained from National Institutes of Health (NIH), USA) at $10^{5.0}$TCID$_{50}$/ml (0.5 ml orally and 0.25 ml per nostril).

Blood samples were collected a day prior to first series of vaccinations, a day prior to second series of vaccinations, just prior to challenge, at three weeks post challenge and weekly thereafter for 8 consecutive weeks. The blood samples were tested for FeLV antigenemia using a commercial kit (Virachek®, Synbiotics Corp.) to detect free, soluble p27 protein. Antigenemia was considered persistent when a kitten tested positive for 3 consecutive weeks or 5 non-consecutive weeks.

FeLV Antigenemia:

In the group 1, five kittens had persistent antigenemia (75% of protection). In the group 2, 18 kittens had persistent antigenemia, corresponding to 90% of the kittens.

The statistical analysis of these results showed a significant difference between groups 1 and 2 (p=6.861E-05).

Clinical Signs:

None of the kittens in any group were anorexic during the observation period.

With the exception of one kitten in the control group, none of the kittens showed signs of depression.

None of the kittens showed injection site reactions.

CONCLUSION

The recombinant viral vaccine injected with needle-free injector was safe in kittens based upon the absence of anorexia and depression and virtually no local reaction.

The recombinant viral vaccine protected kittens against FeLV challenge when compared to unvaccinated control group.

The protection obtained after needle-free vaccination is higher than those obtained after vaccination with syringe and needle (see example 2), about 75% of protection compared to 65% respectively, even though the quantity of injected recombinant viral vaccine comprising canarypox vector expressing FeLV env and gag/pol genes are 2 times lower for the primo-administration and 6 times lower for the boost administration.

The invention shall now be further described by the following numbered paragraphs:

1. The use of an efficient amount of a recombinant viral vector encoding and expressing at least one FeLV immunogen and of an acceptable vehicle or diluent, for the preparation of a liquid recombinant viral vaccine designed to be administered to animals of the felidae family using a liquid jet needle-free injector and to elicit a safe and protective immune response against FeLV.
2. A use according to the paragraph 1, wherein the vaccine comprises a viral vector selected among the members of the group consisting of herpesvirus, adenovirus, poxvirus.
3. A use according to the paragraph 2, wherein the viral vector is a canarypox virus or a fowipox virus.
4. A use according to the paragraph 2, wherein the viral vector is vCP97.
5. A use according to the paragraph 1, wherein the vaccine contains from about $10^{4.5}$ to about $10^{7.0}$ TCID$_{50}$/dose (50% tissue culture infective dose per dose of vaccine).
6. A use according to the paragraph 1, wherein the liquid jet needle-free injector is a Vitajet™ device.
7. A vaccination kit or set, comprising a liquid jet needle-free injector and at least one vaccine vial containing a FeLV recombinant vaccine based on a viral vector, operatively assembled to perform the administration of the vaccine to a animal of the felidae family and to elicit a safe and protective immune response against FeLV.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of eliciting a safe and protective immune response against FeLV comprising administering a vaccine comprising an effective amount of a recombinant avipox vector containing and expressing an exogenous nucleotide sequence encoding at least one FeLV immunogen and an acceptable vehicle or diluent, to a felidae with a liquid jet needle-free injector, wherein the vaccine comprises from about $10^{4.5}$ to about $10^{7.0}$ TCID$_{50}$/dose.
2. The method according to claim 1, wherein the avipox vector is a canarypox virus or a fowlpox virus.
3. The method according to claim 2 wherein the avipox is a canarypox virus.
4. The method according to claim 3 wherein the canarypox virus is ALVAC.
5. The method according to claim 3, wherein the canarypox virus is vCP97.
6. The method according to claim 1 wherein the at least one FeLV antigen is an env protein.
7. The method according to claim 1 wherein the at least one FeLV antigen is a gag/pol protein.
8. The method according to claim 1 wherein the liquid jet needle-free injector has 1 to 10 nozzles.
9. The method according to claim 1 wherein the liquid jet needle-free injector has 1 to 6 nozzles.
10. A vaccination kit or set, comprising a liquid jet needle-free injector and at least one vaccine vial containing a vaccine consisting of a recombinant canarypox virus that contains and expresses in vivo a nucleic acid molecule encoding a FeLV antigen and a veterinarily acceptable carrier, operatively assembled to perform the administration of the vaccine to an animal of the felidae family and to elicit a safe and protective immune response against FeLV, wherein the vaccine comprises from about $10^{4.5}$ to about $10^{7.0}$ TCID$_{50}$/dose.
11. The vaccination kit or set according to claim 10 wherein the viral vector is a canarypox virus.
12. The vaccination kit or set according to claim 11 wherein the canarypox virus is ALVAC.
13. The vaccination kit or set according to claim 11, wherein the canarypox virus is vCP97.
14. The vaccination kit or set according to claim 10 wherein the at least one FeLY antigen is an env protein.
15. The vaccination kit or set according to claim 10 wherein the at least one FeLV antigen is a gag/pol protein.
16. The vaccination kit or set according to claim 10, wherein the liquid jet needle-free injector has 1 10 nozzles.
17. The vaccination kit or set according to claim 10 wherein the liquid jet needle-free injector has 1 to 6 nozzles.
18. The vaccination kit or set according to claim 10 wherein the vaccine comprises a dosage volume of about 0.1 ml to about 1.0 ml.

* * * * *